(12) United States Patent
Keranen et al.

(10) Patent No.: US 11,195,613 B2
(45) Date of Patent: Dec. 7, 2021

(54) BOOKMARKING CAPABILITY FOR RADIATION TREATMENT PLANNING AND MANAGEMENT

(71) Applicants: Varian Medical Systems International AG, Steinhausen (CH); Varian Medical Systems, Inc., Palo Alto, CA (US)

(72) Inventors: Wayne Keranen, Palo Alto, CA (US); Beat Markwalder, Steinhausen (CH); Marco Meier, Steinhausen (CH); Michael Waschbuesch, Steinhausen (CH)

(73) Assignees: Varian Medical Systems International AG, Steinhausen (CH); Varian Medical Systems, Inc., Palo Alto, CA (US)

( * ) Notice: Subject to any disclaimer, the term of this patent is extended or adjusted under 35 U.S.C. 154(b) by 73 days.

(21) Appl. No.: 16/369,649

(22) Filed: Mar. 29, 2019

(65) Prior Publication Data

US 2020/0312449 A1 Oct. 1, 2020

(51) Int. Cl.
*G16H 40/60* (2018.01)
*G16H 50/20* (2018.01)
(Continued)

(52) U.S. Cl.
CPC .............. *G16H 40/60* (2018.01); *A61N 5/103* (2013.01); *G06F 16/9562* (2019.01);
(Continued)

(58) Field of Classification Search
CPC ...... G06F 19/00; G06F 16/9562; G06T 11/20; G06T 19/20; G06T 7/12; G06T 7/174;
(Continued)

(56) References Cited

U.S. PATENT DOCUMENTS

| | | | |
|---|---|---|---|
| 8,860,717 B1* | 10/2014 | Zeiger | G06T 15/503 345/419 |
| 2005/0049500 A1* | 3/2005 | Babu | A61B 8/13 600/443 |

(Continued)

OTHER PUBLICATIONS

Dang, et.al., "Informatics in Radiology", (2009) Radiographics, vol. 29: pp. 1-17. (Year: 2009).*

*Primary Examiner* — Robert A Sorey
(74) *Attorney, Agent, or Firm* — Fitch, Even, Tabin & Flannery LLP

(57) ABSTRACT

A control circuit operably couples to a memory having a plurality of different radiation treatment applications stored therein, a data store having patient data stored therein, and at least a first user interface comprising a first display and a first user input interface. The control circuit can be configured to present simultaneously, via the first display and for a given patient, at least two workspaces that each correspond to a different one of the radiation treatment applications wherein the workspaces are using patient data from the data store for the given patient. The control circuit can also be configured to present, via the user input interface, a bookmark capture opportunity, such that a user of the apparatus can selectively create a bookmark that captures a present state for both of the at least two workspaces and hence for the radiation treatment applications that correspond to the at least two workspaces.

16 Claims, 4 Drawing Sheets

(51) Int. Cl.
*A61N 5/10* (2006.01)
*G06F 16/955* (2019.01)

(52) U.S. Cl.
CPC ..... *G16H 50/20* (2018.01); *A61N 2005/1041* (2013.01); *A61N 2005/1074* (2013.01)

(58) Field of Classification Search
CPC .. G16H 40/20; G16H 50/20; G06Q 50/22–24; A61N 5/103; A61N 2005/1041; A61N 2005/1074
See application file for complete search history.

(56) References Cited

U.S. PATENT DOCUMENTS

| | | | |
|---|---|---|---|
| 2008/0002811 A1* | 1/2008 | Allison | A61N 5/1049 378/65 |
| 2010/0053208 A1* | 3/2010 | Menningen | G06T 19/00 345/619 |
| 2017/0195377 A1* | 7/2017 | Ahmed | H04L 51/04 |
| 2019/0046813 A1* | 2/2019 | Zhou | G16H 50/70 |

* cited by examiner

BOOKMARKING CAPABILITY FOR RADIATION TREATMENT PLANNING AND MANAGEMENT

TECHNICAL FIELD

These teachings relate generally to radiation treatment planning and management systems.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called treatment plan often serves in the foregoing regards.

A treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Radiation treatment planning and management systems serve, at least in part, to facilitate the development of one or more radiation treatment plans and the corresponding management of such plans. That management can include, but is not limited to, creating a treatment plan, setting up the radiation delivery context (for example, by ensuring that all delivery fields are properly configured), and managing the radiation delivery process. The applicants have determined that such a system can be further configured to deliver additional content and interactive capabilities to facilitate tumor boards, chart rounds, peer review of contouring and planning, and treatment planning conferences, to note but a few examples.

Unfortunately, with increased capabilities and flexibility comes increased user confusion and training requirements. Such complexity can be further exacerbated by application settings that employ two or more active displays to present such content and/or where sequential presentations of content are desired. Furthermore, the applicants have determined that in a typical application setting these various capabilities would be facilitated by different radiation treatment applications and the corresponding segregated workspaces presented on one or more active displays. Such concerns can discourage attempts to develop and/or utilize such a multifaceted system.

BRIEF DESCRIPTION OF THE DRAWINGS

The above needs are at least partially met through provision of the bookmarking capability for radiation treatment planning and management system described in the following detailed description, particularly when studied in conjunction with the drawings, wherein.

Figure 1:
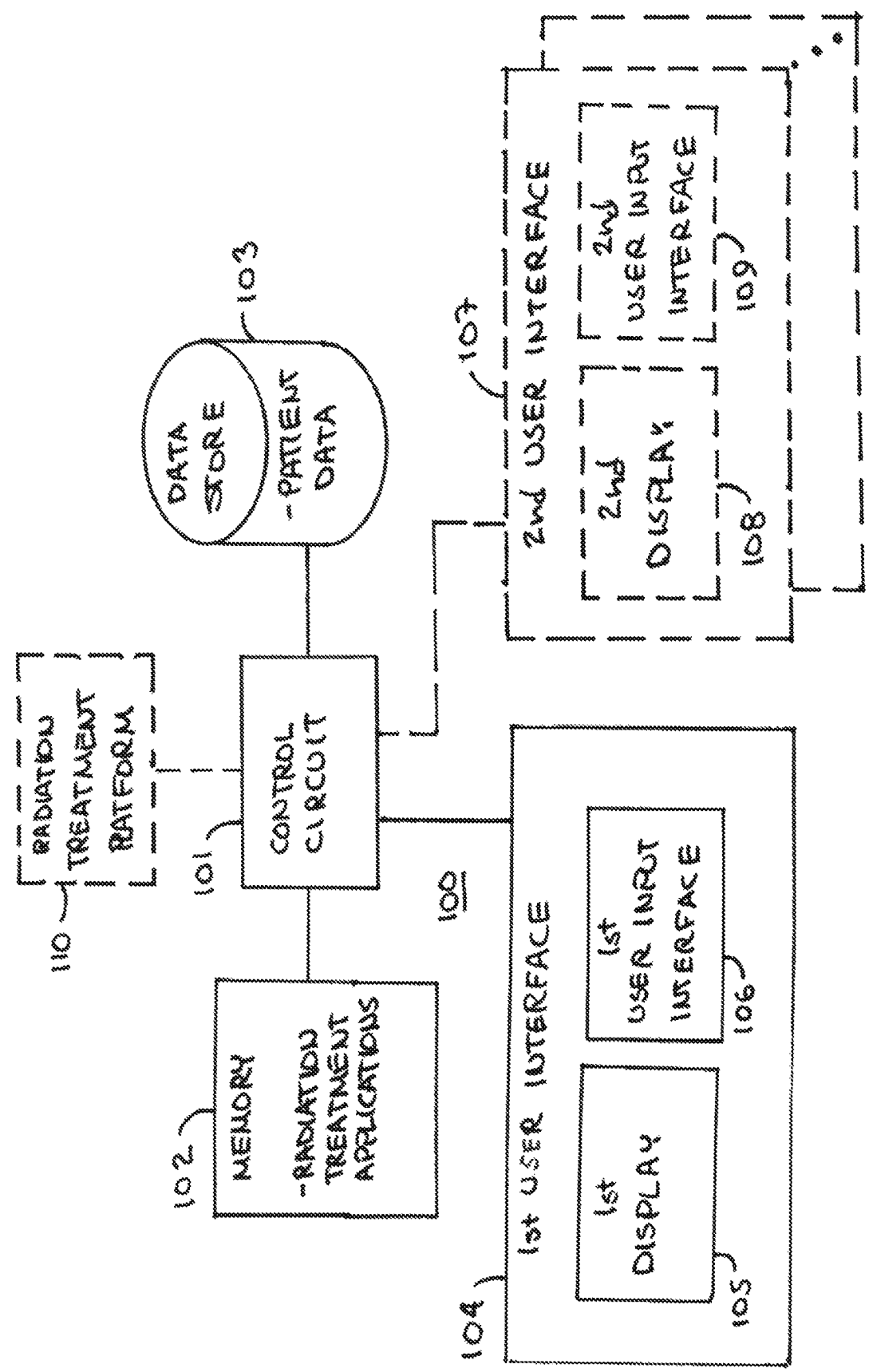
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments a control circuit operably couples to a memory having a plurality of different radiation treatment applications stored therein (including, for example, a radiation prescription application and a contouring application), a data store having patient data stored therein, and at least a first user interface comprising a first display and a first user input interface. The control circuit is configured to present simultaneously, via the first display and for a given patient, at least two workspaces that each correspond to a different one of the radiation treatment applications wherein the workspaces are using patient data from the data store for the given patient. The control circuit is also configured to present, via the user input interface, a bookmark capture opportunity, such that a user of the apparatus can selectively create a bookmark that captures a present state for both of the at least two workspaces and hence for the radiation treatment applications that correspond to the at least two workspaces.

These teachings are highly flexible in practice and can readily scale to accommodate, for example, two, three, four, or more user interfaces that each comprise at least a corresponding display. Notwithstanding the presence and use of a significant plurality of displays, the aforementioned bookmark capture opportunity can still serve to create a bookmark that captures a present state for all of the workspaces supported by all of the displays.

By one approach, the control circuit can be further configured to include with the bookmark capture opportunity an automatic capture of at least one thumbnail image that represents the present state for the two or more applicable workspaces.

By one approach the control circuit can be further configured to present, via the one or more provided user input interfaces, a bookmark recall opportunity, such that a user of the apparatus can selectively recall a bookmark to thereby present, via at least the first display (and other displays when provided and utilized) the captured present state for all of the applicable workspaces that correspond to the captured bookmark. By one approach the control circuit can be configured to respond to assertion of such a bookmark recall opportunity by driving the radiation treatment applications that correspond to the two or more workspaces to a precise state, using patient data for the given patient, that corresponds to the captured present state, such that a user of the apparatus can selectively edit inputs to a selected one of the radiation treatment applications following assertion of the bookmark recall opportunity.

So configured, a relatively complex multi-application and multi-workspace application setting (utilizing one or more displays), which multiplicity of applications may or may not be integrated or even aware and/or intraoperative with one another, can benefit from the above-described bookmark capability in a relatively simple and even substantially intuitive manner. By one approach such a bookmarking capability can be leveraged to facilitate preparing a scene-by-scene presentation that employs concatenated bookmarks to present potentially complex multi-application results and/or processing in a simple and intuitive manner.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises a physical structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

In this example the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to the radiation treatment applications referenced herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

In this example the control circuit 101 also operably couples to a data store 103 that stores patient data. Examples of such data include but are not limited to identifying information for individual patients, medical history information, CT scans and other imaging data, information regarding previously-administered radiation dosages, and so forth. Those skilled in the art will understand and appreciate that this data store 103 can be physically and logically discrete from the aforementioned memory 102 or may be partially or wholly a physical and logical part of that memory 102 as desired.

In this example the control circuit 101 further operably couples to a first user interface 104. This first user interface 104 includes a first display 105 and a first user input interface 106. The latter can comprise any of a variety of user-input mechanisms (such as, but not limited to, keyboards and keypads, cursor-control devices, touch-sensitive displays, speech-recognition interfaces, gesture-recognition interfaces, and so forth). It will be understood that the first display 105 and the first user input interface 106 can be physically integrated if desired (as when the first display 105 also comprises a touch-sensitive display).

These teachings will accommodate also operably coupling the control circuit 101 to a plurality of user interfaces, including a second user interface 107 through an Nth user interface as desired (where "N" is an integer greater than 2). This second user interface 107 can include at least a second display 108 and/or a second user input interface 109, as can each of the additional user interfaces, as desired. As a more specific example, the control circuit 101 could operably couple to two displays, three displays, or four displays (or more) as desired. Such a plurality of displays, when employed and as one illustrative example, can be positioned in a shared presentation area (for example, at a single workstation area utilized by a single user).

By one optional approach the control circuit 101 also operably couples to a radiation treatment platform 110 configured to deliver therapeutic radiation to a corresponding patient. These teachings are generally applicable for use with any of a wide variety of radiation treatment platforms. In a typical application setting the radiation treatment platform 110 will include an x-ray source. The x-ray source can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons. A typical radiation treatment platform 110 may also include one or more support surfaces (such as a couch) to support the patient during the treatment session, a gantry or other mechanism to permit selective movement of the x-ray source, and one or more components (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
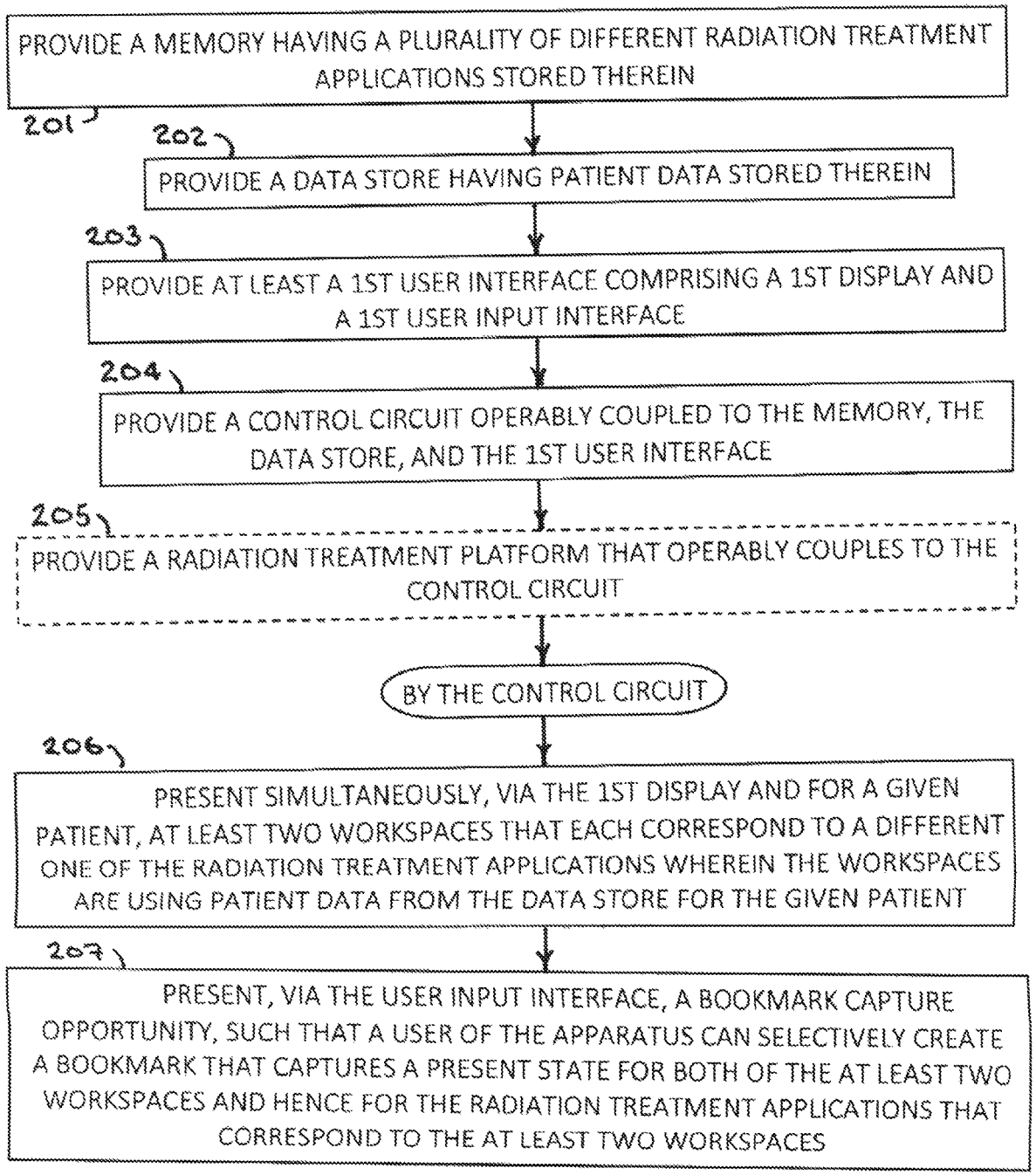
FIG. 2 comprises a flow diagram as configured in accordance with various embodiments of these teachings.

With continued reference to FIG. 1, and referring now as well to FIG. 2, a corresponding process 200 that comports with these teachings will be presented.

At block 201 this process 200 provides a memory (such as the above-described memory 102) having a plurality of different radiation treatment applications toward therein. Examples in these regards include, but are not limited to, radiation treatment plan optimization applications, radiation prescription applications, one or more contouring applications, external beam applications, and so forth. Generally speaking, this collection of radiation treatment applications can pertain to any of developing, reviewing, administering, monitoring, and/or otherwise managing the radiation-based treatment of a patient. Also generally speaking, these radiation treatment applications are configured to be compatibly processed and utilized by the aforementioned control circuit 101.

At block 202, this process 200 also provides a data store (such as the above-described data store 103) having patient data stored therein. This data may pertain to only a single patient or may comprise data for a plurality of individual patients, where the patient data correlates in each instance to a particular one of the many patients. (These teachings will also accommodate, if desired, patient data that represents an aggregation of a plurality of patients, perhaps in an anonymized form.) Examples of patient data include but are not limited to various kinds and modalities of imaging information, contouring and segmentation data, treatment prescriptions, radiation dosing histories and/or dose volume histograms, diagnostic information, and so forth.

At block 203, this process provides at least a first user interface comprising a first display and a first user input interface (for example, as described above with reference to FIG. 1). Depending upon the needs and/or opportunities presented by a given application setting, this step can include providing two or more additional user interfaces that each have at least one corresponding display and which may have their own user input interfaces. Accordingly, this process 200 will accommodate an application setting having only a single display, only two displays, only three displays, only four displays, and so forth as desired.

If desired, any given display can be utilized by the control circuit 101 to simultaneously display content corresponding to one or more of the aforementioned radiation treatment applications. For example, a first one of the displays can present content only for a first one of the radiation treatment applications while a second one of the displays simultaneously presents content only for a second, different one of the radiation treatment applications. As another example, the control circuit 101 can partition the presentation area of one or more of the displays into two or more workspaces, where each workspace serves to present contact for only a corresponding one of the radiation treatment applications. Accordingly, and as an illustrative example not intended to suggest any particular limitations, a first such display can be partitioned into two workspaces that simultaneously present, respectively, content for a first and second radiation treatment application while a second such display is partitioned into two workspaces that simultaneously present, respectively, content for a third and fourth radiation treatment application. (As another example, the first such display could be partitioned into two workspaces that simultaneously present, respectively, first content using first data for the first radiation treatment application and second content using second data for that same first radiation treatment application, where the first data is different from the second data.)

So configured, a user having visual access to a presentation zone that includes such displays can have simultaneous visual access to any of a plurality of active radiation treatment applications. The user can also interact with such radiation treatment applications via one or more of the user input interfaces described above. The radiation treatment applications may be configured to interact with one another (such that, for example, changing a parameter in one of the applications will cause a corresponding change in another of the applications) or not as desired.

At block 204, this process 200 provides a control circuit (such as the control circuit 101 described above) that operably couples to the above described memory, data store, and user interface or user interfaces. And, if desired, at optional block 205 this process 200 can further provide a radiation treatment platform (such as the radiation treatment platform 110 described above) that also operably couples to the control circuit.

The remaining steps, functions, and activities described for this process 200 can be carried out, for example, by the control circuit 101.

At block 206 the control circuit 101 presents, simultaneously and via at least the first display 105 or via a plurality of such displays, at least two workspaces as described above. Generally speaking, each workspace constitutes a physical region on each display that is essentially dedicated to a corresponding application. These regions can be specifically denoted (using, for example, a "window" paradigm or other boundary indicator) as desired. (Those skilled in the art will understand that dedicating a particular physical region on a display to a particular corresponding application does not necessarily preclude also accommodating, at least temporarily, other bits of information (such as so-called widgets or submenus).) As noted above, these teachings will accommodate using a plurality of displays and each display may itself be configured to accommodate two or more such workspaces. Accordingly, these teachings will accommodate great flexibility and an ability to accommodate a considerable number and variety of simultaneously displayed radiation treatment applications.

Figure 3:
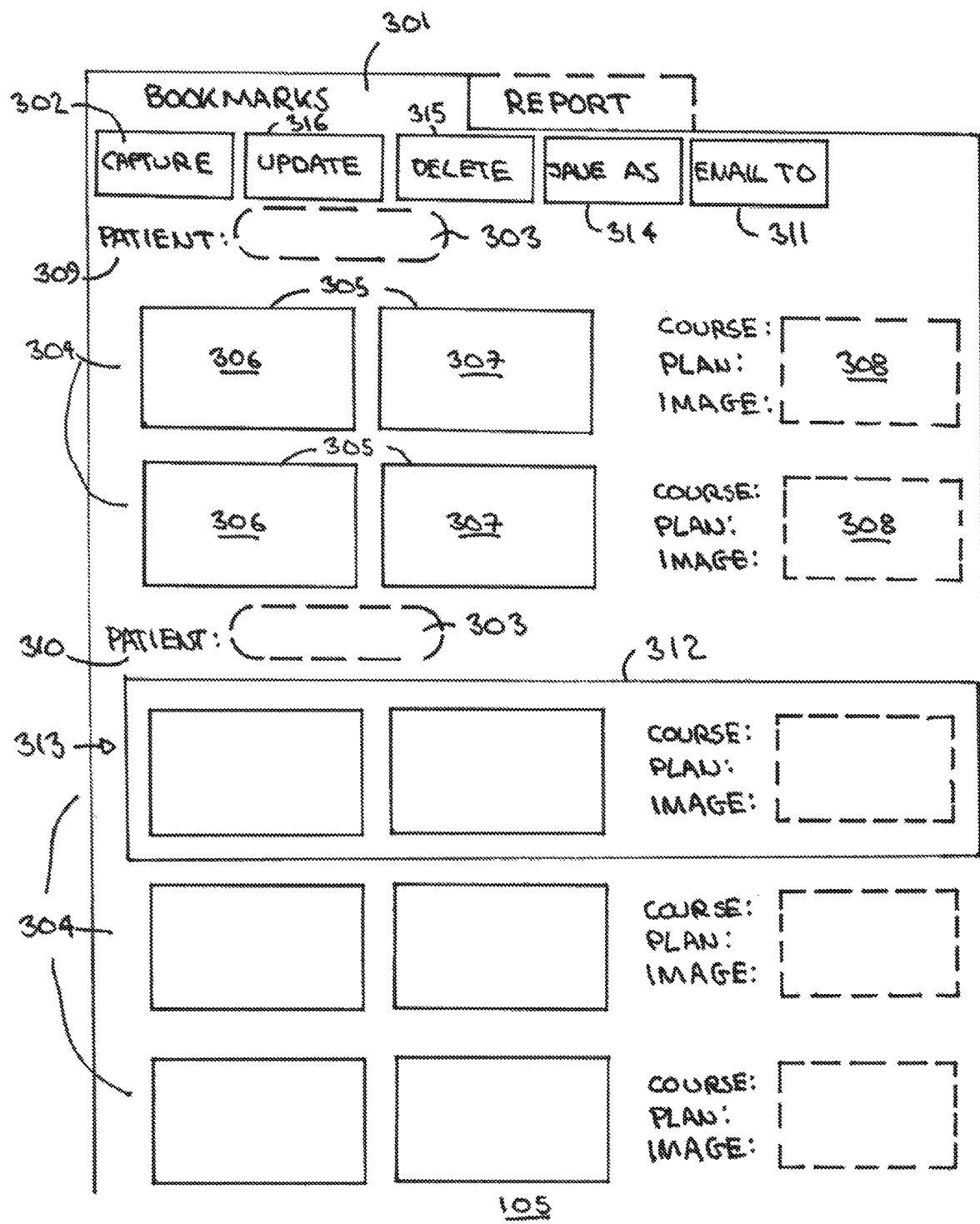
FIG. 3 comprises a schematic screen shot as configured in accordance with various embodiments of these teachings.

At block 207, the control circuit 101 also presents, via at least one of the user input interfaces, a bookmark capture opportunity, such that a user of the apparatus 100 can selectively create a bookmark that captures a present state for both (or some, or all) of the two or more workspaces and hence for the radiation treatment applications that correspond to such workplaces. Referring momentarily to FIG. 3, an illustrative example in these regards will now be presented. It shall be understood that the specific details of this illustrative example are not intended to suggest any particular limitations with respect to these teachings.

FIG. 3 presents a schematic screen shot of at least a portion of, in this example, the aforementioned first display 105. The presented image includes a tabbed area 301 to support the bookmark capability described herein. So configured, by selecting this tabbed area 301 (by, for example, clicking or tapping the "bookmark" tab itself) the various displays, content, and buttons corresponding to this capability are presented.

The aforementioned bookmark capture opportunity comprises, in this example, a "capture" button 302 (this button comprising a soft or virtual button). Asserting this capture button 302 creates a bookmark that captures the aforementioned present state for the various workspaces that represent the active radiation treatment applications.

By one approach, this activity can also include an automatic capture of a thumbnail image representing the present state for all of the corresponding workspaces. For the sake of clarity and simplicity, this example presumes only two active applications/workspaces (which may be contained within a single display or which may be parsed out over two displays as desired). Accordingly, for a first patient (identified in a first patient identifier field 303), each assertion of the bookmark capture opportunity 302 leads to a bookmark 304 having two thumbnail images 305 (with a first thumbnail image 306 that corresponds to the first radiation treatment application workspace and a second thumbnail image 307 that corresponds to the second radiation treatment application workspace).

If desired, each bookmark 304 can include other information such as, in this example, an information field 308 to present information corresponding to the relevant course, plan, and image (or any other context information that can help and serve to quickly and easily identify the bookmark).

In the illustrated example, there are two captured bookmarks 304 for a first patient 309 and three captured bookmarks 304 for a second patient 310. By one approach, a screen scrolling capability can be utilized to permit, for example, the user to scroll downwardly, upwardly, and/or sideways as appropriate to see additional bookmarks/patients.

Figure 4:
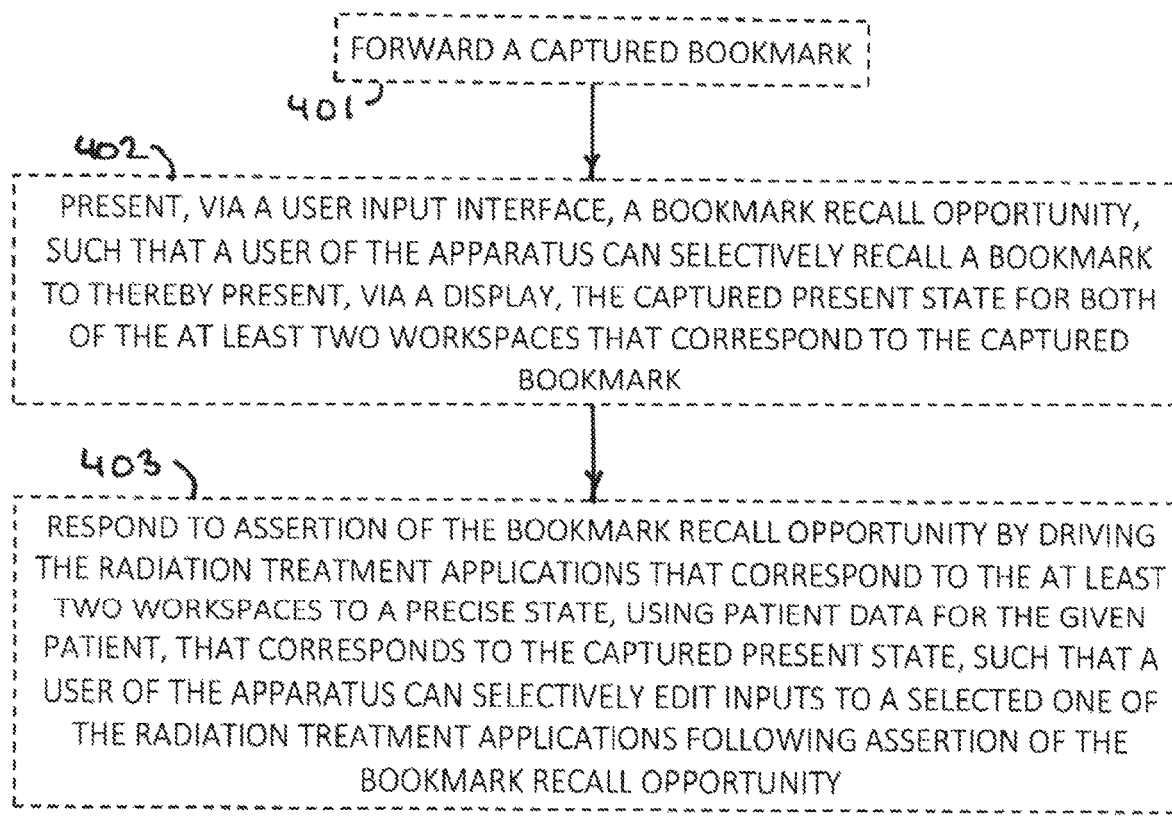
FIG. 4 comprises a flow diagram as configured in accordance with various embodiments of these teachings.

With continued reference to FIG. 3 and with further reference to FIG. 4, by one optional approach and as specified at block 401, the control circuit 101 can provide for forwarding a captured bookmark. This might include, as suggested in FIG. 3, a button 311 that, when asserted by the user, serves to create an email to forward part or all of the contents of a selected bookmark 304. Other forwarding capabilities can be utilized in a similar manner, such as a multimedia messaging service, facsimile transmissions, and so forth.

At optional block 402, this process 200 can provide for having the control circuit 101 present, via the aforementioned user input interface, a bookmark recall opportunity. So configured, a user assertion of the bookmark recall opportunity can selectively recall a bookmark to thereby present, via the display or displays, the captured present state for all of the workspaces that correspond to the captured bookmark. With specific reference to FIG. 3, this bookmark recall opportunity could be selected by, for example, asserting either of the thumbnail images 306, 307 for a selected one of the bookmarks 304.

By one approach, recalling a particular bookmark includes driving the corresponding applications to the bookmark state using presently-available patient data. As a result, if the patient data has changed from when the bookmark was originally created, the displayed application state can actually differ accordingly. In such a case, the stored bookmark information would not be merely a stored screen shot for each of the workspaces, but instead would comprise information to allow the bookmark system to drive the respective applications to the context/state at the point when the bookmark was created.

By one approach, a currently selected bookmark 313 can be identified or marked as being currently selected using, in this example, a distinctive border 312. This border 312 might be a simple line, or that is distinguished by use of a particular color or other visual treatment. These teachings will also accommodate, if desired, other visually-perceptive indicium such as an overlying color that includes all or most of the bookmark 304.

These teachings are highly flexible in practice and will accommodate a variety of supplemental capabilities and/or modifications to suit various application setting opportunities or requirements. As but one example in these regards, and with continued reference to FIG. 4, at optional block 403 the control circuit 101 can respond to assertion of the aforementioned bookmark recall opportunity by driving the radiation treatment applications that correspond to the captured workspaces to a precise state, using patient data for the given patient, that corresponds to the captured present state. So configured, a user of the apparatus 100 can selectively edit inputs to a selected one of the radiation treatment applications following assertion of the bookmark recall opportunity to effectively move forward from that particular point to explore, for example, a different treatment approach than had been previously considered.

If desired, and as shown in FIG. 3, these teachings will accommodate providing a user opportunity to save a selected bookmark 304 as a file or other data item separate and apart from serving as a bookmark, per se. In this illustrative example a "save as" button 314 serves in these regards. Asserting this button 314 can permit the bookmark content to be saved, for example, to the aforementioned memory 102, data store 103, or some other data repository of choice including selected cloud storage.

Also as shown in FIG. 3, these teachings will accommodate providing a "delete" button 315 to permit the user to delete a selected bookmark 304 and/or an "update" button 316 to provide a way to open an editing or other modification paradigm for a selected bookmark 304.

These teachings permit a user to bookmark a precise state for a plurality of applications, to store that bookmark, and then to later restore the bookmark application states at a later time. Such a capability can be leveraged in various ways. As one useful example, a plurality of bookmarks can be chained together to create corresponding presentations that are delivered on any number of displays by a single user navigating through the previously created presentation. Interestingly, such a presentation can span application states across a plurality of different patients. Such presentations can greatly facilitate the activities of tumor boards, chart rounds, peer reviews of contouring and planning, as well as any of a variety of oncology-based conferences (such as radio therapy conferences including treatment planning conferences).

As another example, the bookmarking capability described herein can be used to save the state of a plurality of applications at the close of the business day and to then restore those states the next day to permit the user to quickly return to their work.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. As one example in these regards, these teachings can be applied beyond use with radiation treatment applications to encompass, for example, cancer care in a more generalized sense (to thereby provide similar benefits in the areas of surgery, chemotherapy, and other approaches to cancer treatment).

What is claimed is:

1. An apparatus comprising:
   a memory having a plurality of different radiation treatment applications stored therein;
   a data store having patient data stored therein;
   at least a first user interface comprising a first display and a first user input interface;
   a control circuit operably coupled to the memory, the data store, and the first user interface, the control circuit being configured to:
   present simultaneously, via the first display and for a given patient, at least two workspaces that each correspond to a different one of the radiation treatment applications wherein the workspaces are using patient data from the data store for the given patient;
   present, via the user input interface, a bookmark capture opportunity, such that a user of the apparatus can selectively create a bookmark that captures a present state for both of the at least two workspaces and hence for the radiation treatment applications that correspond to the at least two workspaces;
   present, via the first user input interface, a bookmark recall opportunity, such that a user of the apparatus can selectively recall a bookmark;
   respond to assertion of the bookmark recall opportunity by driving the radiation treatment applications that correspond to the at least two workspaces to a precise state, using patient data for the given patient that has changed from when the bookmark was originally created, such that the precise state is different from the present state that corresponds to the bookmark at a point when the bookmark was created; and
   a radiation treatment platform that operably couples to the control circuit to thereby receive and implement a radiation treatment plan from the control circuit by administering corresponding therapeutic radiation to the given patient.

2. The apparatus of claim 1 further comprising:
   at least a second user interface comprising a second display;
   and wherein the control circuit operably couples to the second user interface and wherein the control circuit is configured to:
   present simultaneously, via the first and the second display and for a given patient, at least two workspaces that each correspond to a different one of the radiation treatment applications wherein the workspaces are using patient data from the data store for the given patient.

3. The apparatus of claim 2 further comprising:
   at least a third user interface comprising a third display and a fourth user interface comprising a fourth display;
   and wherein the control circuit operably couples to the third and fourth user interface and wherein the control circuit is configured to:
   present simultaneously, via the first, second, third, and fourth display and for a given patient, a plurality of workspaces that each correspond to a different one of the radiation treatment applications wherein the workspaces are using patient data from the data store for the given patient.

4. The apparatus of claim 1 wherein the plurality of different radiation treatment applications include a radiation prescription application and a contouring application.

5. The apparatus of claim 1 wherein the control circuit is further configured to include with the bookmark capture opportunity an automatic capture of a thumbnail image representing the present state for both of the at least two workspaces.

6. The apparatus of claim 1 wherein the control circuit is further configured to:
   present, via the first user input interface, a bookmark recall opportunity, such that a user of the apparatus can selectively recall a bookmark to thereby present, via the first display, the captured present state for both of the at least two workspaces that correspond to the captured bookmark.

7. The apparatus of claim 6 wherein the control circuit is further configured to:
   respond to assertion of the bookmark recall opportunity by driving the radiation treatment applications that correspond to the at least two workspaces to a precise state, using patient data for the given patient, that corresponds to the captured present state, such that a user of the apparatus can selectively edit inputs to a selected one of the radiation treatment applications following assertion of the bookmark recall opportunity.

8. The apparatus of claim 6 wherein the control circuit is further configured to:
   forward a captured bookmark via email.

9. A method comprising:
   providing a memory having a plurality of different radiation treatment applications stored therein;
   providing a data store having patient data stored therein;
   providing at least a first user interface comprising a first display and a first user input interface;
   providing a control circuit operably coupled to the memory, the data store, and the first user interface;
   employing the control circuit to:
   present simultaneously, via the first display and for a given patient, at least two workspaces that each correspond to a different one of the radiation treatment applications wherein the workspaces are using patient data from the data store for the given patient; and
   present, via the user input interface, a bookmark capture opportunity, such that a user of the apparatus can selectively create a bookmark that captures a present state for both of the at least two workspaces and hence for the radiation treatment applications that correspond to the at least two workspaces;
   present, via the first user input interface, a bookmark recall opportunity, such that a user of the apparatus can selectively recall a bookmark;
   respond to assertion of the bookmark recall opportunity by driving the radiation treatment applications that correspond to the at least two workspaces to a precise state, using patient data for the given patient that has changed from when the bookmark was originally created, such that the precise state is different from the present state that corresponds to the bookmark at a point when the bookmark was created; and
   providing a radiation treatment platform that operably couples to the control circuit to thereby receive and implement a radiation treatment plan from the control circuit by administering corresponding therapeutic radiation to the given patient.

10. The method of claim 9 further comprising:
    providing at least a second user interface comprising a second display that operably couples to the control circuit;
    and wherein the control circuit is further employed to:
    present simultaneously, via the first and the second display and for a given patient, at least two workspaces that each correspond to a different one of the radiation treatment applications wherein the workspaces are using patient data from the data store for the given patient.

11. The method of claim 10 further comprising:
providing at least a third user interface comprising a third display and a fourth user interface comprising a fourth display that operably couple to the control circuit;
and wherein the control circuit is further employed to:
present simultaneously, via the first, second, third, and fourth display and for a given patient, a plurality of workspaces that each correspond to a different one of the radiation treatment applications wherein the workspaces are using patient data from the data store for the given patient.

12. The method of claim 9 wherein the plurality of different radiation treatment applications include a radiation prescription application and a contouring application.

13. The method of claim 9 further comprising including with the bookmark capture opportunity an automatic capture of a thumbnail image representing the present state for both of the at least two workspaces.

14. The method of claim 9 further comprising, by the control circuit:
presenting, via the first user input interface, a bookmark recall opportunity, such that a user of the apparatus can selectively recall a bookmark to thereby present, via the first display, the captured present state for both of the at least two workspaces that correspond to the captured bookmark.

15. The method of claim 14 further comprising, by the control circuit:
responding to assertion of the bookmark recall opportunity by driving the radiation treatment applications that correspond to the at least two workspaces to a precise state, using patient data for the given patient, that corresponds to the captured present state, such that a user of the apparatus can selectively edit inputs to a selected one of the radiation treatment applications following assertion of the bookmark recall opportunity.

16. The method of claim 14 further comprising, by the control circuit:
forwarding a captured bookmark via email.

\* \* \* \* \*